US010611706B2

(12) United States Patent
Al-Dughaither et al.

(10) Patent No.: US 10,611,706 B2
(45) Date of Patent: Apr. 7, 2020

(54) METHOD OF SEPARATING HEXENE

(71) Applicant: SABIC Global Technologies B.V., Bergen op Zoom (NL)

(72) Inventors: Abdullah Saad Al-Dughaither, Riyadh (SA); Shahid Azam, Riyadh (SA); Adel Saeed Al-Dossari, Riyad (SA); Abdulmajeed Mohammed Al-Hamdan, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/065,901

(22) PCT Filed: Dec. 28, 2016

(86) PCT No.: PCT/IB2016/058062
§ 371 (c)(1),
(2) Date: Jun. 25, 2018

(87) PCT Pub. No.: WO2017/115308
PCT Pub. Date: Jul. 6, 2017

(65) Prior Publication Data
US 2019/0010101 A1 Jan. 10, 2019

Related U.S. Application Data

(60) Provisional application No. 62/273,021, filed on Dec. 30, 2015.

(51) Int. Cl.
*C07C 7/04* (2006.01)
*B01D 3/14* (2006.01)
(Continued)

(52) U.S. Cl.
CPC .............. *C07C 7/04* (2013.01); *B01D 3/14* (2013.01); *C08F 110/02* (2013.01); *C10G 7/00* (2013.01)

(58) Field of Classification Search
CPC ... C07C 7/04; B01D 3/14; C08F 110/02; C10G 7/00
(Continued)

(56) References Cited

U.S. PATENT DOCUMENTS 2,700,061 A   1/1955   Owen
3,356,590 A   12/1967  Johnson
(Continued)

FOREIGN PATENT DOCUMENTS

EP   0590883 B1   11/1996

OTHER PUBLICATIONS

International Search Report for International Application No. PCT/IB2016/058062; dated Mar. 31, 2017; 6 pages.
(Continued)

*Primary Examiner* — Ling Siu Choi
*Assistant Examiner* — Ronald Grinsted
(74) *Attorney, Agent, or Firm* — Cantor Colburn LLP

(57) ABSTRACT

A method of producing hexene includes: passing a feed stream comprising $C_1$ to $C_{24}$ hydrocarbons through a distillation column, wherein a reflux ratio of the distillation column is greater than or equal to 1.33; distributing a light fraction comprising $C_4$-$C_6$ hydrocarbons to a top portion of the distillation column; distributing a heavy fraction comprising $C_8$-$C_{12}$ hydrocarbons to a bottom portion of the distillation column; and withdrawing a top product comprising hexene from the distillation column.

20 Claims, 2 Drawing Sheets

(51) Int. Cl.
*C10G 7/00* (2006.01)
*C08F 110/02* (2006.01)

(58) Field of Classification Search
USPC .......................................................... 526/77
See application file for complete search history.

(56) References Cited

U.S. PATENT DOCUMENTS

| | | |
|---|---|---|
| 3,428,528 A | 2/1969 | Oglesby, Jr. et al. |
| 5,332,426 A | 7/1994 | Tang et al. |
| 5,853,551 A | 12/1998 | Boucot et al. |
| 2007/0185362 A1 | 8/2007 | Lattner et al. |
| 2014/0012059 A1 | 1/2014 | Vinel et al. |
| 2015/0291486 A1 | 10/2015 | Weber et al. |
| 2015/0299069 A1* | 10/2015 | Azam ................... C07C 2/36 585/513 |
| 2019/0002373 A1* | 1/2019 | Al-Dughaither .......... C07C 7/04 |
| 2019/0010100 A1* | 1/2019 | Al-Dughaither .......... C07C 7/04 |

OTHER PUBLICATIONS

Written Opinion of the International Search Report for International Application No. PCT/IB2016/058062; dated Mar. 31, 2017; 7 pages.

* cited by examiner

METHOD OF SEPARATING HEXENE

CROSS REFERENCE TO RELATED APPLICATIONS

This application is a 371 of International Application No. PCT/M2016/058062, filed Dec. 28, 2016, which claims priority to U.S. Application No. 62/273,021, filed Dec. 30, 2015, both of which are incorporated herein by reference in their entirety.

BACKGROUND

Hexene remains an important and commercially valuable product in the petrochemical industry. For example, 1-hexene comonomer can be copolymerized with ethylene to produce a flexible form of polyethylene. Another use of 1-hexene is the production of the linear aldehyde heptanal via 1-hexene hydroformylation.

Hexene is often isolated from a mixture of several different hydrocarbons. For example, hexene is often separated from other hydrocarbons through the use of a distillation tower. These conventional hexene isolation methods result in significant impurities in the hexene product. Accordingly, additional processing and purification procedures must take place. These additional processes are often costly and highly inefficient.

Thus, there is a need for an efficient method of isolating hexene from a hydrocarbon mixture that results in a product with minimal impurities and does not require costly purification procedures.

SUMMARY

Disclosed, in various embodiments, are processes and systems for producing hexene.

A method of producing hexene, comprises: passing a feed stream comprising $C_1$ to $C_{24}$ hydrocarbons through a distillation column, wherein a reflux ratio of the distillation column is greater than or equal to 1.33; distributing a light fraction comprising $C_4$-$C_6$ hydrocarbons to a top portion of the distillation column; distributing a heavy fraction comprising $C_8$-$C_{12}$ hydrocarbons to a bottom portion of the distillation column; and withdrawing a top product comprising hexene from the distillation column.

A method of producing hexene, comprises: passing a feed stream comprising 1-hexene, 1-octene, 1-butene, water, and toluene through a distillation column, wherein a reflux ratio of the distillation column is 1.35 to 1.40; distributing a light fraction comprising 1-hexene and 1-butene to a top portion of the distillation column; distributing a heavy fraction comprising 1-octene and toluene to a bottom portion of the distillation column; withdrawing a top product comprising hexene from the distillation column, wherein the top product comprises less than or equal to 1 parts per million toluene; and withdrawing a bottom product comprising 1-octene and toluene from the distillation column.

A system for producing hexene, comprises: a distillation column comprising a top portion; and a bottom portion; wherein the distillation column is configured to: separate a feed stream into a light fraction and a heavy fraction, wherein a reflux ratio of the distillation column is greater than or equal to 1.33; distribute the light fraction to the top portion of the distillation column, wherein the light fraction comprises $C_4$-$C_6$ hydrocarbons; distribute the heavy fraction to the bottom portion of the distillation column, wherein the heavy fraction comprises $C_8$-$C_{12}$ hydrocarbons; and release a top product from the top portion of the distillation column, wherein the top product comprises hexene.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
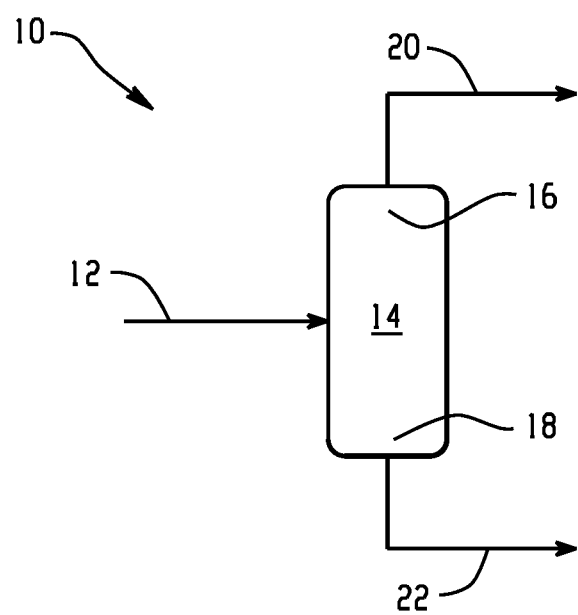
FIG. 1 is a simplified schematic diagram representing a hexene separation method in accordance with the present disclosure.

The method disclosed herein can provide an efficient method of isolating hexene from a hydrocarbon mixture that results in a product with minimal impurities and without costly purification procedures. For example, the method disclosed herein can produce an overhead 1-hexene product with less than or equal to 1 parts per million toluene impurity. The method disclosed herein also does not use additional fractionation units or adsorber units to purify the hexene product. Accordingly, the method disclosed herein saves significant amounts of capital, energy, and other resources as compared to conventional methods. The method disclosed herein can be efficiently applied to an already exiting distillation column. The method disclosed herein can also leave column parameters such as pressure and temperature unaffected. The method disclosed herein can produce an important and commercially valuable product in the petrochemical industry. For example, 1-hexene comonomer can be copolymerized with ethylene to produce a flexible form of polyethylene. Another use of 1-hexene is the production of the linear aldehyde heptanal via 1-hexene hydroformylation.

1-Hexene is commonly manufactured by two general routes: (i) full-range processes via the oligomerization of ethylene and (ii) on-purpose technology. A minor route to 1-hexene, used commercially on smaller scales, is the dehydration of hexanol. Prior to the 1970s, 1-hexene was also manufactured by the thermal cracking of waxes. Linear internal hexenes were manufactured by chlorination/dehydrochlorination of linear paraffins.

"Ethylene oligomerization" combines ethylene molecules to produce linear alpha-olefins of various chain lengths with an even number of carbon atoms. This approach results in a distribution of alpha-olefins.

Fischer-Tropsch synthesis to make fuels from synthesis gas derived from coal can recover 1-hexene from the aforementioned fuel streams, where the initial 1-hexene concentration cut can be 60% in a narrow distillation, with the remainder being vinylidenes, linear and branched internal olefins, linear and branched paraffins, alcohols, aldehydes, carboxylic acids, and aromatic compounds. The trimerization of ethylene by homogeneous catalysts has been demonstrated.

There are a wide range of applications for linear alpha olefins. The lower carbon numbers, 1-butene, 1-hexene and 1-octene can be used as comonomers in the production of polyethylene. High density polyethylene (HDPE) and linear low density polyethylene (LLDPE) can use approximately 2-4% and 8-10% of comonomers, respectively.

Another use of $C_4$-$C_8$ linear alpha olefins can be for production of linear aldehyde via oxo synthesis (hydroformylation) for later production of short-chain fatty acid, a carboxylic acid, by oxidation of an intermediate aldehyde, or linear alcohols for plasticizer application by hydrogenation of the aldehyde.

An application of 1-decene is in making polyalphaolefin synthetic lubricant basestock (PAO) and to make surfactants in a blend with higher linear alpha olefins.

$C_{10}$-$C_{14}$ linear alpha olefins can be used in making surfactants for aqueous detergent formulations. These carbon numbers can be reacted with benzene to make linear alkyl benzene (LAB), which can be further sulfonated to linear alkyl benzene sulfonate (LABS), a popular relatively low cost surfactant for household and industrial detergent applications.

Although some $C_{14}$ alpha olefin can be sold into aqueous detergent applications, $C_{14}$ has other applications such as being converted into chloroparaffins. A recent application of $C_{14}$ is as on-land drilling fluid basestock, replacing diesel or kerosene in that application. Although $C_{14}$ is more expensive than middle distillates, it has a significant advantage environmentally, being much more biodegradable and in handling the material, being much less irritating to skin and less toxic.

$C_{16}$-$C_{18}$ linear olefins find their primary application as the hydrophobes in oil-soluble surfactants and as lubricating fluids themselves. $C_{16}$-$C_{18}$ alpha or internal olefins are used as synthetic drilling fluid base for high value, primarily off-shore synthetic drilling fluids. The preferred materials for the synthetic drilling fluid application are linear internal olefins, which are primarily made by isomerizing linear alpha-olefins to an internal position. The higher internal olefins appear to form a more lubricious layer at the metal surface and are recognized as a better lubricant. Another application for $C_{16}$-$C_{18}$ olefins is in paper sizing. Linear alpha olefins are, once again, isomerized into linear internal olefins are then reacted with maleic anhydride to make an alkyl succinic anhydride (ASA), a popular paper sizing chemical.

$C_{20}$-$C_{30}$ linear alpha olefins production capacity can be 5-10% of the total production of a linear alpha olefin plant. These are used in a number of reactive and non-reactive applications, including as feedstocks to make heavy linear alkyl benzene (LAB) and low molecular weight polymers used to enhance properties of waxes.

The use of 1-hexene can be as a comonomer in production of polyethylene. High-density polyethylene (HDPE) and linear low-density polyethylene (LLDPE) use approximately 2-4% and 8-10% of comonomers, respectively.

Another use of 1-hexene is the production of the linear aldehyde heptanal via hydroformylation (oxo synthesis). Heptanal can be converted to the short-chain fatty acid heptanoic acid or the alcohol heptanol.

The method disclosed herein for hexene production can include passing a feed stream comprising $C_1$ to $C_{24}$ hydrocarbons through a distillation column. For example, the feed stream can comprise 1-hexene, 1-octene, 1-butene, water, toluene, or a combination comprising at least one of the foregoing. A reflux ratio of the distillation column can be greater than or equal to 1.0, for example, greater than or equal to 1.25, for example, greater than or equal to 1.30, for example, greater than or equal to 1.33. For example, the reflux ratio of the distillation column can be greater than or equal to 1.35. For example, the reflux ratio can be greater than or equal to 1.40. For example, the reflux ratio can be 1.35 to 1.40. The method can include distributing a light fraction comprising $C_4$-$C_6$ hydrocarbons to a top portion of the distillation column. For example, the light fraction can comprise 1-butene, 1-hexene, and water. The method disclosed herein can include distributing a heavy fraction comprising $C_7$-$C_{12}$ hydrocarbons to a bottom portion of the distillation column. For example, the heavy fraction can comprise toluene, 1-octene, or a combination comprising at least one of the foregoing. The method disclosed herein can include withdrawing a top product comprising hexene from the distillation column. The use of a specific reflux ratio can result in a top 1-hexene product of extremely high purity. For example, the top product can comprise less than or equal to 1 parts per million toluene. A bottom product comprising 1-octene, toluene, or a combination comprising at least one of the foregoing can also be withdrawn from the distillation column.

The method disclosed herein for hexene production can include a feed stream. For example, the feed stream can comprise $C_1$ to $C_{24}$ hydrocarbons. For example, the feed stream can comprise $C_1$ to $C_{12}$ hydrocarbons. For example, the feed stream can comprise 1-hexene, 1-octene, 1-butene, water, toluene, ethylene, ethane, propylene, or a combination comprising at least one of the foregoing.

The method disclosed herein can comprise passing as feed stream through a distillation column. The distillation column can comprise a top portion and bottom portion. The distillation column can be a packed bed or trayed distillation column. The distillation column can comprise steel, other metals, ceramics, polymers, or a combination comprising at least one of the foregoing. A reflux ratio of the distillation column can be greater than or equal to 1.33. For example, the reflux ratio of the distillation column can be greater than or equal to 1.35. For example, the reflux ratio can be greater than or equal to 1.40. For example, the reflux ratio can be 1.35 to 1.40. Operating conditions for the distillation column can include a temperature of 80 to 200° C., for example, 85 to 190° C., for example, 88 to 182° C., for example, 90 to 175° C. and a pressure of 3 to 10 barg (0.3 to 1.0 MegaPascals (MPa), for example, 3.5 to 7.5 barg (0.35 to 0.75 MPa), for example, 4 to 4.5 barg (0.4 to 0.45 MPa)).

The method disclosed herein for hexene production can include separating a feed stream into a light fraction and a heavy fraction. For example, the method disclosed herein can include distributing a light fraction to a top portion of a distillation column. For example, the light fraction can comprise $C_4$-$C_6$ hydrocarbons. In the method, a water stream can optionally be included to adjust the flow to result in less $C_7$ hydrocarbons in the light fraction. For example, the water stream can optionally be included to adjust the flow to result in less $C_7$ hydrocarbons in the $C_6$ portion of the light fraction. For example, the light fraction can comprise 1-butene, 1-hexene, water, or a combination comprising at least one of the foregoing. The method disclosed herein can include distributing a heavy fraction to a bottom portion of the distillation column. For example, the heavy fraction can comprise $C_7$-$C_{12}$ hydrocarbons. For example, the heavy fraction can comprise toluene, 1-octene, or a combination comprising at least one of the foregoing.

The method disclosed herein for hexene production can include withdrawing products from the distillation column. For example, a top product can be withdrawn from a top portion of the distillation column. For example, the top product can comprise a light fraction comprising $C_4$-$C_6$ hydrocarbons. For example, the top product can comprise 1-hexene, 1-butene, water, or a combination comprising at least one of the foregoing. The top product can comprise less than or equal to 100 parts per million toluene by weight. For example, the top product can comprise less than or equal to 1 parts per million toluene by weight. The method disclosed herein can include withdrawing a bottom product from a bottom portion of the distillation column. For example, the bottom product can comprise a heavy fraction comprising $C_7$-$C_{12}$ hydrocarbons. For example, the bottom product can comprise toluene, 1-octene, or a combination comprising at least one of the foregoing.

The method disclosed herein for hexene production can produce an important and commercially valuable product in the petrochemical industry. For example, 1-hexene comonomer can be copolymerized with ethylene to produce a flexible form of polyethylene. Another use of 1-hexene can be the production of the linear aldehyde heptanal via 1-hexene hydroformylation.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to FIG. 1, the method disclosed herein for hexene production 10 can include passing a feed stream 12 comprising $C_1$ to $C_{24}$ hydrocarbons through a distillation column 14. For example, the feed stream can comprise 1-hexene, 1-octene, 1-butene, water, toluene, or a combination comprising at least one of the foregoing. A reflux ratio of the distillation column can be greater than or equal to 1.0, for example, greater than or equal to 1.25, for example, greater than or equal to 1.30, for example, greater than or equal to 1.33. For example, the reflux ratio of the distillation column can be greater than or equal to 1.35. For example, the reflux ratio can be greater than or equal to 1.40. For example, the reflux ratio can be 1.35 to 1.40, for example, 1.33. The method can include distributing a light fraction comprising $C_4$-$C_6$ hydrocarbons to a top portion 16 of the distillation column 14. For example, the light fraction can comprise 1-butene, 1-hexene, water, or a combination comprising at least one of the foregoing. The method disclosed herein can include distributing a heavy fraction comprising $C_7$-$C_{12}$ hydrocarbons to a bottom portion 18 of the distillation column 14. For example, the heavy fraction can comprise toluene, 1-octene, or a combination comprising at least one of the foregoing. The method disclosed herein 10 can include withdrawing a top product 20 comprising hexene from the distillation column 14. The use of a specific reflux ratio can result in a top 1-hexene product 20 of extremely high purity. For example, the top product 20 can comprise less than or equal to 1 parts per million toluene. A bottom product 22 comprising 1-octene, toluene, or a combination comprising at least one of the foregoing can also be withdrawn from the distillation column 14. Table 1 lists various possible operating conditions and components of the stream numbers in reference to FIG. 1.

TABLE 1

| | Stream number (in reference to FIG. 1) | | |
|---|---|---|---|
| | 12 | 20 | 22 |
| Temperature (° C.) | 58.8 | 57.6 | 180 |
| Pressure (barg) (MPa) | 4.2 (0.42) | 3.99 (0.399) | 4.25 (0.425) |
| Component mass fraction | | | |
| Ethylene | 3.20E−05 | 0.000128 | 6.43E−20 |
| Ethane | 6.00E−06 | 2.40E−05 | 5.19E−20 |
| Propylene | 2.00E−06 | 8.00E−06 | 5.57E−18 |
| 1-Butene | 0.135541 | 0.542248 | 4.48E−10 |
| 1-Hexene | 0.114363 | 4.57E−01 | 0.000317 |
| Toluene | 0.711701 | 4.56E−05 | 0.951767 |
| 1-Octene | 0.03583 | 4.46E−08 | 0.047917 |
| Water | 0.002525 | 0.000971 | 1.36E−31 |

The following example is merely illustrative of the hexene production method disclosed herein and is not intended to limit the scope hereof. Unless otherwise stated, all examples were based upon simulations.

EXAMPLES

Example 1

Figure 2:
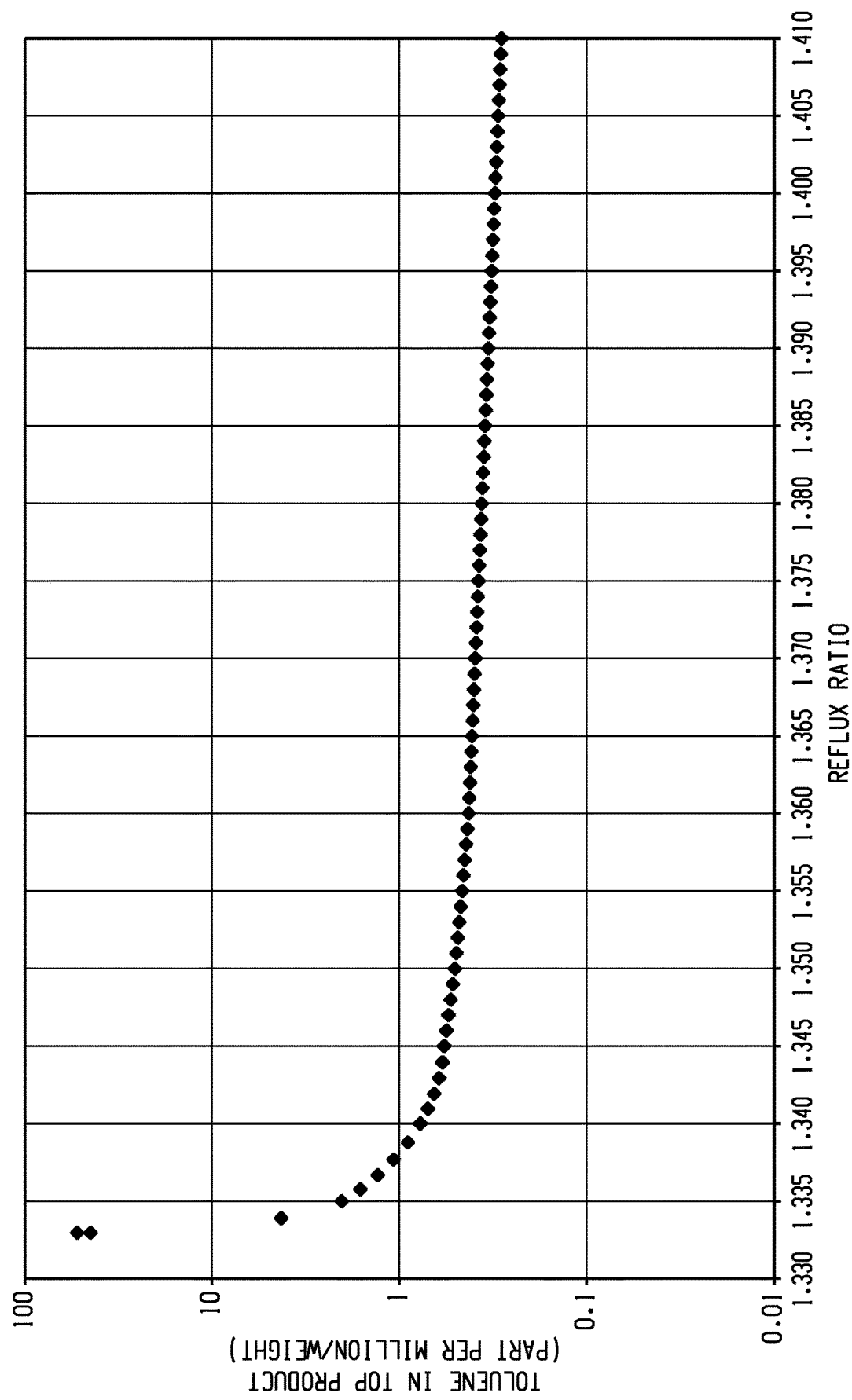
FIG. 2 is a graph depicting the relationship between reflux ratio and top product toluene levels in accordance with the present disclosure.

A method for hexene production in accordance with the present disclosure 10, and as depicted in FIG. 1, is used for the purposes of this example. Computer simulations of the hexene production method 10 are conducted using process calculation software. Table 2 lists the processing conditions and stream components. A feed stream comprising 1-hexene, 1-octene, 1-butene, water, and toluene is fed to a distillation column. The reflux ratio of the distillation column is varied from 1.33 to 1.41. A top product is withdrawn from the distillation column comprising 1-hexene. The results of the simulation are presented in FIG. 2. FIG. 2 is a graph depicting the relationship between reflux ratio and top product toluene levels in accordance with the present disclosure. The toluene levels in the top product are given in parts per million by weight. As can be seen, the use of a particular reflux ratio results in a top 1-hexene product of extremely high purity. For example, toluene concentration in the top product is below the mutual solubility of hydrocarbons. For example, at a reflux ratio of 1.35 to 1.4, the top product can comprise less than or equal to 1 parts per million toluene.

TABLE 2

| | Stream number (in reference to FIG. 1) | | |
|---|---|---|---|
| | 12 | 20 | 22 |
| Temperature (° C.) | 58.8 | 57.6 | 180 |
| Pressure (barg) (MPa) | 4.2 (0.42) | 3.99 (0.399) | 4.25 (0.425) |
| Component mass fraction | | | |
| Ethylene | 3.20E−05 | 0.000128 | 6.43E−20 |
| Ethane | 6.00E−06 | 2.40E−05 | 5.19E−20 |
| Propylene | 2.00E−06 | 8.00E−06 | 5.57E−18 |
| 1-Butene | 0.135541 | 0.542248 | 4.48E−10 |
| 1-Hexene | 0.114363 | 4.57E−01 | 0.000317 |
| Toluene | 0.711701 | 4.56E−05 | 0.951767 |
| 1-Octene | 0.03583 | 4.46E−08 | 0.047917 |
| Water | 0.002525 | 0.000971 | 1.36E−31 |

The processes and systems disclosed herein include(s) at least the following embodiments:

Embodiment 1

A method of producing hexene, comprising: passing a feed stream comprising $C_1$ to $C_{24}$ hydrocarbons through a distillation column, wherein a reflux ratio of the distillation column is greater than or equal to 1.33; distributing a light fraction comprising $C_4$-$C_6$ hydrocarbons to a top portion of the distillation column; distributing a heavy fraction comprising $C_8$-$C_{12}$ hydrocarbons to a bottom portion of the distillation column; and withdrawing a top product comprising hexene from the distillation column.

Embodiment 2

The method of Embodiment 1, wherein the feed stream comprises $C_1$ to $C_{12}$ hydrocarbons.

Embodiment 3

The method of any of the preceding embodiments, wherein the feed stream comprises ethylene, ethane, propylene, butene, hexene, toluene, octene, water, or a combination comprising at least one of the foregoing.

Embodiment 4

The method of any of the preceding embodiments, wherein the distillation column is a packed bed distillation column.

Embodiment 5

The method of any of the preceding embodiments, wherein the reflux ratio of the distillation column is greater than or equal to 1.35.

Embodiment 6

The method of Embodiment 5, wherein the reflux ratio of the distillation column is greater than or equal to 1.36.

Embodiment 7

The method of Embodiment 5, wherein the reflux ratio of the distillation column is 1.35 to 1.40.

Embodiment 8

The method of any of the preceding embodiments, wherein a temperature within the distillation column is 85° C. to 200° C.

Embodiment 9

The method of any of the preceding embodiments, wherein a pressure within the distillation column is 0.4 MegaPascals to 0.45 MegaPascals.

Embodiment 10

The method of any of the preceding embodiments, wherein the light fraction comprises butene and the heavy fraction comprises octene.

Embodiment 11

The method of any of the preceding embodiments, wherein the top product comprises less than or equal to 45 parts per million toluene.

Embodiment 12

The method of Embodiment 11, wherein the top product comprises less than or equal to 1 parts per million toluene.

Embodiment 13

The method of any of the preceding embodiments, wherein the top product comprises 1 to 99 weight percent hexene.

Embodiment 14

The method of any of the preceding embodiments, further comprising withdrawing a bottom product comprising octene and toluene from the distillation column.

Embodiment 15

The method of any of the preceding embodiments, further comprising polymerizing the top product to produce polyethylene.

Embodiment 16

The method of any of the preceding embodiments, wherein the method is free of absorber units.

Embodiment 17

The method of any of the preceding embodiments, wherein energy consumption of the distillation column is reduced by 5% as compared to a distillation column operated by a different method.

Embodiment 18

A method of producing hexene, comprising: passing a feed stream comprising 1-hexene, 1-octene, 1-butene, water, and toluene through a distillation column, wherein a reflux ratio of the distillation column is 1.35 to 1.40; distributing a light fraction comprising 1-hexene and 1-butene to a top portion of the distillation column; distributing a heavy fraction comprising 1-octene and toluene to a bottom portion of the distillation column; withdrawing a top product comprising hexene from the distillation column, wherein the top product comprises less than or equal to 1 parts per million toluene; and withdrawing a bottom product comprising 1-octene and toluene from the distillation column.

Embodiment 19

The method of Embodiment 18, further comprising polymerizing the top product to produce polyethylene.

Embodiment 20

The method of any of Embodiments 18-19, wherein the method is free of absorber units.

Embodiment 21

A system for producing hexene, comprising: a distillation column comprising a top portion; and a bottom portion;

wherein the distillation column is configured to: separate a feed stream into a light fraction and a heavy fraction, wherein a reflux ratio of the distillation column is greater than or equal to 1.33; distribute the light fraction to the top portion of the distillation column, wherein the light fraction comprises $C_4$-$C_6$ hydrocarbons; distribute the heavy fraction to the bottom portion of the distillation column, wherein the heavy fraction comprises $C_8$-$C_{12}$ hydrocarbons; and release a top product from the top portion of the distillation column, wherein the top product comprises hexene.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$) alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing hexene, comprising:
passing a feed stream comprising $C_1$ to $C_{24}$ hydrocarbons through a distillation column, wherein a reflux ratio of the distillation column is greater than or equal to 1.33;
distributing a light fraction comprising $C_4$-$C_6$ hydrocarbons to a top portion of the distillation column;
distributing a heavy fraction comprising $C_8$-$C_{12}$ hydrocarbons to a bottom portion of the distillation column; and
withdrawing a top product comprising hexene from the distillation column.

2. The method of claim 1, wherein the feed stream comprises $C_1$ to $C_{12}$ hydrocarbons.

3. The method of claim 1, wherein the feed stream comprises ethylene, ethane, propylene, butene, hexene, toluene, octene, water, or a combination comprising at least one of the foregoing.

4. The method of claim 1, wherein the distillation column is a packed bed distillation column.

5. The method of claim 1, wherein the reflux ratio of the distillation column is greater than or equal to 1.35.

6. The method of claim 5, wherein the reflux ratio of the distillation column is greater than or equal to 1.36.

7. The method of claim 5, wherein the reflux ratio of the distillation column is 1.35 to 1.40.

8. The method of claim 1, wherein a temperature within the distillation column is 85° C. to 200° C.

9. The method of claim 1, wherein a pressure within the distillation column is 0.4 MegaPascals to 0.45 MegaPascals.

10. The method of claim 1, wherein the light fraction comprises butene and the heavy fraction comprises octene.

11. The method of claim 1, wherein the top product comprises less than or equal to 45 parts per million toluene.

12. The method of claim 1, wherein the top product comprises 1 to 99 weight percent hexene.

13. The method of a claim 1, further comprising withdrawing a bottom product comprising octene and toluene from the distillation column.

14. The method of claim 1, further comprising polymerizing the top product to produce polyethylene.

15. The method of claim 1, wherein the method is free of absorber units.

16. The method of claim 1, wherein energy consumption of the distillation column is reduced by 5% as compared to a distillation column operated by a different method.

17. A method of producing hexene, comprising:
   passing a feed stream comprising 1-hexene, 1-octene, 1-butene, water, and toluene through a distillation column, wherein a reflux ratio of the distillation column is 1.35 to 1.40;
   distributing a light fraction comprising 1-hexene and 1-butene to a top portion of the distillation column;
   distributing a heavy fraction comprising 1-octene and toluene to a bottom portion of the distillation column;
   withdrawing a top product comprising hexene from the distillation column, wherein the top product comprises less than or equal to 1 parts per million toluene; and
   withdrawing a bottom product comprising 1-octene and toluene from the distillation column.

18. The method of claim 17, further comprising polymerizing the top product to produce polyethylene.

19. The method of claim 17, wherein the method is free of absorber units.

20. A system for producing hexene, comprising:
   a distillation column comprising
      a top portion; and
      a bottom portion;
   wherein the distillation column is configured to:
      separate a feed stream into a light fraction and a heavy fraction, wherein a reflux ratio of the distillation column is greater than or equal to 1.33;
      distribute the light fraction to the top portion of the distillation column, wherein the light fraction comprises $C_4$-$C_6$ hydrocarbons;
      distribute the heavy fraction to the bottom portion of the distillation column, wherein the heavy fraction comprises $C_8$-$C_{12}$ hydrocarbons; and
      release a top product from the top portion of the distillation column, wherein the top product comprises hexene.

* * * * *